US012036135B2

(12) United States Patent
Castro (10) Patent No.: US 12,036,135 B2
(45) Date of Patent: Jul. 16, 2024

(54) BIOCOMPATIBLE CONSTRUCTION FOR IMPLANTATION INTO A JOINT

(71) Applicant: Blue Sky Technologies, LLC, Louisville, KY (US)

(72) Inventor: Frank Castro, Louisville, KY (US)

(73) Assignee: BLUE SKY TECHNOLOGIES, LLC, Louisville, KY (US)

( * ) Notice: Subject to any disclaimer, the term of this patent is extended or adjusted under 35 U.S.C. 154(b) by 336 days.

(21) Appl. No.: 17/638,826

(22) PCT Filed: Oct. 3, 2020

(86) PCT No.: PCT/US2020/054166
§ 371 (c)(1),
(2) Date: Feb. 27, 2022

(87) PCT Pub. No.: WO2021/162754
PCT Pub. Date: Aug. 19, 2021

(65) Prior Publication Data
US 2022/0273463 A1 Sep. 1, 2022

Related U.S. Application Data

(60) Provisional application No. 62/975,244, filed on Feb. 12, 2020.

(51) Int. Cl.
*A61F 2/46* (2006.01)
*A61B 17/16* (2006.01)
*A61F 2/44* (2006.01)

(52) U.S. Cl.
CPC ........ *A61F 2/4644* (2013.01); *A61B 17/1671* (2013.01); *A61F 2/4405* (2013.01); *A61F 2/4455* (2013.01); *A61F 2/447* (2013.01); *A61F 2/4611* (2013.01); *A61F 2002/4627* (2013.01); *A61F 2002/4649* (2013.01)

(58) Field of Classification Search
CPC .... A61F 2/4644; A61F 2/4405; A61F 2/4455; A61F 2/447; A61F 2002/4627; A61F 2002/4649; A61B 17/1671
See application file for complete search history.

(56) References Cited

U.S. PATENT DOCUMENTS

| | | |
|---|---|---|
| 6,770,096 B2 | 8/2004 | Bolger et al. |
| 8,366,774 B1 | 2/2013 | Bruffey et al. |
| 9,421,112 B2 | 8/2016 | Bal et al. |
| 2009/0054988 A1 | 2/2009 | Hess |
| 2011/0054530 A1 | 3/2011 | Lins |
| 2014/0088715 A1 | 3/2014 | Ciupik |
| 2014/0094918 A1 | 4/2014 | Vishnubholta et al. |
| 2019/0131417 A1 | 10/2019 | Castro |

FOREIGN PATENT DOCUMENTS

WO    WO-2019018014 A1 *    1/2019    ......... A61B 17/7002

* cited by examiner

*Primary Examiner* — Nicholas J Plionis
(74) *Attorney, Agent, or Firm* — BUSINESS PARENT LAW, PLLC (57) ABSTRACT

A biocompatible construction adapted for use in joint surgeries. Among other things, the joint implant has an anterior cutting edge and a rotatable cutter distinct from the cutting edge. The rotatable cutter allows for graduated cutting of biological tissue or structure.

24 Claims, 5 Drawing Sheets

BIOCOMPATIBLE CONSTRUCTION FOR IMPLANTATION INTO A JOINT

PRIORITY

Applicant claims priority to PCT/US2020/054166—Biocompatible Construction for Implantation into a Joint—filed Oct. 3, 2020 that claimed the benefit of US Provisional Application No. 62/975,244—Biocompatible Construction for Implantation into a Joint—filed Feb. 12, 2020.

BACKGROUND OF THE INVENTION

A. Field of the Invention

The present invention is an implant for a joint or a surgically created cavity. Among other things, the biocompatible construction for implantation into a joint or surgically created cavity has an anterior cutting edge as well as a rotatable cutter. Preferred embodiments of the biocompatible construction include a rotatable cutter with windows disposed between a first and second sections of the rotatable cutter. Select preferred embodiments of the rotatable cutter can be provided with sections that are curvilinear through multiple planes.

B. Description of the Previous Art

Any discussion of references cited in this Description of the Previous Art merely summarizes the disclosures of the cited references and Applicant makes no admission that any cited reference or portion thereof is relevant prior art. Applicant reserves the right to challenge the accuracy, relevancy and veracity of the cited references.

References that may indicate a state-of-the-art include: 1) U.S. Pat. No. 6,770,096—Bolger, et al. that discloses an interbody spinal stabilization cage and spinal stabilization method; 2) U.S. Pat. No. 8,366,774—Bruffey, et al. discloses a spinal cage having deployable member; 3) US Published Patent Application No. 20140094918—Vishnubholta, et al. discloses a stand-alone interbody fixation system; 4) U.S. Pat. No. 9,421,112—Bal, et al. discloses a fixation system for spinal cages; and 5) US Published Patent Application No. 20110054530—Lins discloses a surgical implant device for the translation and fusion of a facet joint of the spine.

Among other things, none of the above listed references disclose a biocompatible construction with a rotatable cutter including comprising: a stub axle (310) engaging the socket (180); a connector (330), engaging the bearing (180), connectable to a device adapted to rotate the cutter (330); first and second sections (350, 400) on opposite sides of the longitudinal axis (X-X); the first and second sections (350, 400) extending lengthwise between the stub axle (180) and the connector (330), wherein each section (350, 400) comprises: a blade (356, 406) to cut the biological structure and a noncutting edge (358, 408) opposed from the blade (356, 406); and a curvature (362, 410) between a first lengthwise end (352, 412) and an opposed second lengthwise end (354, 414) of the noncutting edge (358, 408), wherein, relative to the longitudinal axis (X-X), the opposed noncutting edge (358, 308) curves from a first point more proximate to the longitudinal axis (X-X) to a second point more distant from the longitudinal axis (X-X).

SUMMARY OF THE INVENTION

The more tools or instruments inserted into a surgical field, the greater the possibility of an error resulting in patient injury. Due to the simplicity of the current biocompatible construction, a number of surgical tools required and steps associated with performing prior state-of-the-art fusions can be eliminated. Among other things, use of the current invention allows arthrodesis procedures to be performed in the cervical spine, sacroiliac joint, ankle, hand or other similar joints.

One of the currently available state-of-the art techniques for cervical fusions is the DTRAX system. The DTRAX spinal system uses five instruments, a working cannula, and numerous steps. A working cannula with a chisel is used to breach the desired posterior facet joint. Once in position, the chisel is removed and a broach is inserted through the working cannula. The broach is advanced and retracted several times in order to remove the cartilaginous end-plates. After the broach is removed from the working cannula, a drill is inserted. After drilling is completed, a second rasp is placed to decorticate the posterior cortex. After the use of the second rasp is completed, the fixation device (filled with graft material) is inserted through the working cannula into the joint. Additional graft material is then impacted behind the implant.

Current state-of-the-art sacroiliac surgical procedures require a fusion device that is either inserted from a posterior or lateral approach. Applicant's understanding is: there are fusion devices for use with either the posterior approach or the lateral approach, but the same fusion device is incapable for use with both the posterior and the lateral approaches. Many of the current sacroiliac fusion procedures require the use of working cannulas, numerous broaches, rasps, drills and other devices that tend to complicate the surgical procedure. Applicant's current biocompatible construction can accomplish sacroiliac fusions through either a posterior or lateral approach with fewer surgical tools and steps.

Unlike other joint implants, among other things, the present biocompatible construction can include a rotatable cutter with first and second sections that are curvilinear through multiple planes. Such structures can provide for graduated cutting of structures such as bone and other tissues. Preferred embodiments of the cutter include a stub axle, connector and windows.

An aspect of the present invention is to provide a biocompatible construction with an anterior side having a cutting edge.

Still another aspect of the present invention is to provide a biocompatible construction with an anterior side including a socket.

It is yet another aspect of the present invention to provide a cutter with one or more openings, windows and apertures.

Still another aspect of the present invention is to provide a cutter with a stub axle at one end of the biocompatible construction and a connector at the opposite end of the biocompatible construction.

It is still another aspect of the present invention to provide first and second sections, where relative to the biocompatible construction's longitudinal axis, each section includes a first curvature that curves from a first point more proximate the longitudinal axis toward a second point more distance from the longitudinal axis.

Yet still another aspect of the present invention is to provide a biocompatible construction where rotation of the rotatable cutter causes the first or the second section or both to extend beyond the biocompatible construction.

Still another aspect of the present invention is to provide sections of the rotatable cutter with blades to cut the biological structure or tissue and opposed noncutting edges.

It is still another aspect of the present invention to provide the section's blade with a concave bend relative to the noncutting edge.

Yet another aspect of the present invention is to provide a biocompatible construction that, after insertion into the surgically created opening, provides distraction.

It is yet another aspect of the present invention is to provide a biocompatible construction where, after insertion into the posterior cervical facet joint, the distraction can indirectly provide some neuroforaminal decompression.

It is still another aspect of the present invention to provide a biocompatible construction that can lessen any biocompatible construction subsidence.

Yet still another aspect of the present invention is to provide a biocompatible construction that includes surface treatments. Surface treatments can improve fixation of the biocompatible construction, and it is believed that when the biocompatible construction is inserted at an angle perpendicular to the joint surfaces, surface treatments significantly improve fusion.

A preferred embodiment of the current invention can be described as a biocompatible construction (100) for implantation into a joint or surgically created cavity; the biocompatible construction (100) comprising: a) an anterior side (150) comprising an anterior cutting edge (152) and a socket (180) extending therethrough; b) a surgeon facing side (200), opposite the anterior side (150), comprising a bearing (210); c) a longitudinal axis (X-X) extending through the socket (180) and the bearing (210), wherein lateral openings (130) of the biocompatible construction (100) are outward from the longitudinal axis (X-X); and d) a cutter (300) rotatable about the longitudinal axis (X-X) and adapted to cut a biological structure; the cutter (300) comprising: i) a stub axle (310), surrounding the longitudinal axis (X-X), engaging the socket (180); ii) a connector (330), surrounding the longitudinal axis (X-X) and distinct from the stub axle (310); the connector (330) contacting the bearing (210) and connectable to a device adapted to rotate the cutter (330); iii) windows (320f, 320s) aligned with the longitudinal axis (X-X) and positioned between the stub axle (310) and the connector (330); iv) a first section (350), on a first side of the longitudinal axis (X-X), extending lengthwise between the anterior side (150) and the surgeon facing side (200) and a second section (400), on an opposed second side of the longitudinal axis (X-X), extending lengthwise between the anterior side (150) and the surgeon facing side (200); v) the first section (350) comprising: a first cutting blade (356) to cut the structure and a first noncutting edge (358) opposed from the first cutting blade (356), wherein the first cutting blade (356) comprises a concave bend (390) relative to the opposed first noncutting edge (358); a first curvature (362) between a first lengthwise end (352) and an opposed second lengthwise end (354) of the first noncutting edge (358), wherein, relative to the longitudinal axis (X-X), the first curvature (362) curves from a first point more proximate to the longitudinal axis (X-X) to a second point more distant from the longitudinal axis (X-X); and vi) the second section (400) comprising:

a second cutting blade (406) to cut the structure and a second noncutting edge (408) opposed from the second blade (406), wherein the second blade (406) comprises a concave bend (420) relative to the opposed second noncutting edge (408); and a second curvature (410) between a first lengthwise end (412) and an opposed second lengthwise end (414) of the second noncutting edge (408), wherein, relative to the longitudinal axis (X-X), the second curvature (410) curves from a first point more proximate to the longitudinal axis (X-X) to a second point more distant from the longitudinal axis (X-X).

Another preferred embodiment of the current invention can be described as a biocompatible construction (100) for implantation into a joint or a surgically created cavity; the biocompatible construction (100) comprising: a) an anterior side (150) comprising an anterior cutting edge (152) and a socket (180) extending therethrough; b) a surgeon facing side (200), opposite the anterior side (150), comprising a bearing (210); c) a longitudinal axis (X-X) extending through the socket (180) and the bearing (210), wherein lateral openings (130) of the biocompatible construction (100) are outward from the longitudinal axis (X-X); and d) a cutter (300) rotatable about the longitudinal axis (X-X) and adapted to cut a structure; the cutter (300) comprising: i) a stub axle (310) engaging the socket (180); ii) a connector (330) contacting the bearing (210) and connectable to a device adapted to rotate the cutter (330); iii) first and second interconnected sections (350, 400) on opposite sides of the longitudinal axis (X-X); the first and second interconnected sections (350, 400) extending lengthwise between the anterior side (150) and the surgeon facing side (200), wherein each interconnected section (350, 400) comprises a blade (356, 406) to cut a structure and a noncutting edge (358, 408) opposed from the blade (356, 406); and iv) at least one window (320f) aligned with the longitudinal axis (X-X) and positioned between the stub axle (310) and the connector (330).

Still another preferred embodiment of the current invention can be described as a A biocompatible construction (100) for implantation into a joint or surgically created cavity; the biocompatible construction (100) comprising: a) an anterior side (150) comprising an anterior cutting edge (152) and a socket (180) extending therethrough; the anterior side (150) comprising at least two trapezoidal planes (154f, 154s, 156f, 156s); b) a surgeon facing side (200), opposite the anterior side (150), comprising a bearing (210); c) lateral openings (130) of the biocompatible construction (100) positioned outward from a longitudinal axis (X-X); and d) a rotatable cutter (300) adapted to cut a biological structure; the cutter (300) comprising: i) a stub axle (310) engaging the socket (180); ii) a connector (330), engaging the bearing (180), connectable to a device adapted to rotate the cutter (330); iii) first and second sections (350, 400) on opposite sides of the longitudinal axis (X-X); the first and second sections (350, 400) extending lengthwise between the stub axle (180) and the connector (330), wherein each section (350, 400) comprises:

a blade (356, 406) to cut the biological structure and a noncutting edge (358, 408) opposed from the blade (356, 406); and a curvature (362, 410) between a first lengthwise end (352, 412) and an opposed second lengthwise end (354, 414) of the noncutting edge (358, 408), wherein, relative to the longitudinal axis (X-X), the opposed noncutting edge (358, 308) curves from a first point more proximate to the longitudinal axis (X-X) to a second point more distant from the longitudinal axis (X-X).

It is the novel and unique interaction of these simple elements which creates the system within the ambit of the present invention. Pursuant to the Articles of the Patent Cooperation Treaty and/or Title 35 of the United States Code, select preferred embodiments of the current invention follow. However, it is to be understood that the descriptions of the preferred embodiments do not limit the scope of the present invention.

DESCRIPTION OF THE PREFERRED EMBODIMENTS

Although the disclosure hereof is detailed to enable those skilled in the art to practice the invention, the embodiments published herein merely exemplify the present invention. As used herein, with respect to the biocompatible construction (100): 1) "anterior" of the biocompatible construction (100) means the side of the biocompatible construction most distant from the surgeon and 2) "posterior or surgeon-facing side" of the biocompatible construction (100) means the side of the biocompatible construction nearest the surgeon.

In the most general sense, the present invention can result in joint arthrodesis where the biocompatible construction is surgically inserted into or across a joint space or a surgically created cavity. The current biocompatible construction can be useful for surgeries that can assist in stabilizing injured, deformed and or degenerative joints. Preferred embodiments of the current invention can be employed with ankle, cervical, hand, sacroiliac or other orthopaedic procedures. It appears that the present system is particularly useful for posterior cervical fusions and sacroiliac joint fusions. However, the current invention can also be used to fuse the tibia to the talus, the talus to the calcaneus, and metacarpals to the phalanges.

Preferred embodiments of the current biocompatible constructions can be manufactured of titanium alloys, stainless steel, non-resorbable polymers or any other composition acceptable in the art. Meeting a long felt but unfilled need in the orthopaedic surgical arts, the novel and unique structures of the present biocompatible constructions allow the surgical team to, among other things, simplify previous procedures.

The present invention has an anterior side with an anterior cutting edge and a rotatable cutter about the longitudinal axis of the biocompatible construction. In preferred embodiments, lateral openings of the biocompatible construction are outward from the longitudinal axis. The anterior cutting edge of the biocompatible construction is capable of dissecting through adipose, muscle and/or joint capsule tissues. The rotatable cutter of the implant is capable of cutting cartilage and bone and can be associated with the creation of the surgical cavity. Further, the rotatable cutter can morselize bone in preparation for fusion. The combination of the biocompatible construction's anterior cutting edge and blades meet long felt but unfilled needs in the orthopedic surgical arts: among other things, these novel and unique structures allow the surgeon to simplify the previous operating procedures utilized for posterior cervical, sacroiliac, and other joint fusions.

Devices that insert biocompatible, osteogenic and/or other substances into or out of the interior volume of the biocompatible construction can be used with preferred embodiments of the present invention. The current biocompatible construction is also compatible with flexible drills, fiber optics, vacuums, one or more cannulas and one or more devices for inserting the biocompatible construction. Combinations of one or more of the before identified ancillary devices and the current biocompatible construction can assist with the creation and healing of the surgical wound.

Lateral openings of the biocompatible construction as well as the rotatable cutter's windows and apertures can increase the probability of the osteogenic materials and/or arthrodesis accelerating substances procuring a blood supply. And it is believed that increasing the blood supply to the osteogenic materials held by the biocompatible construction increases the probability of successful fusion. Introduction of osteogenic and other substances into the biocompatible construction can hasten the healing of the surgical wound.

Figure 1:
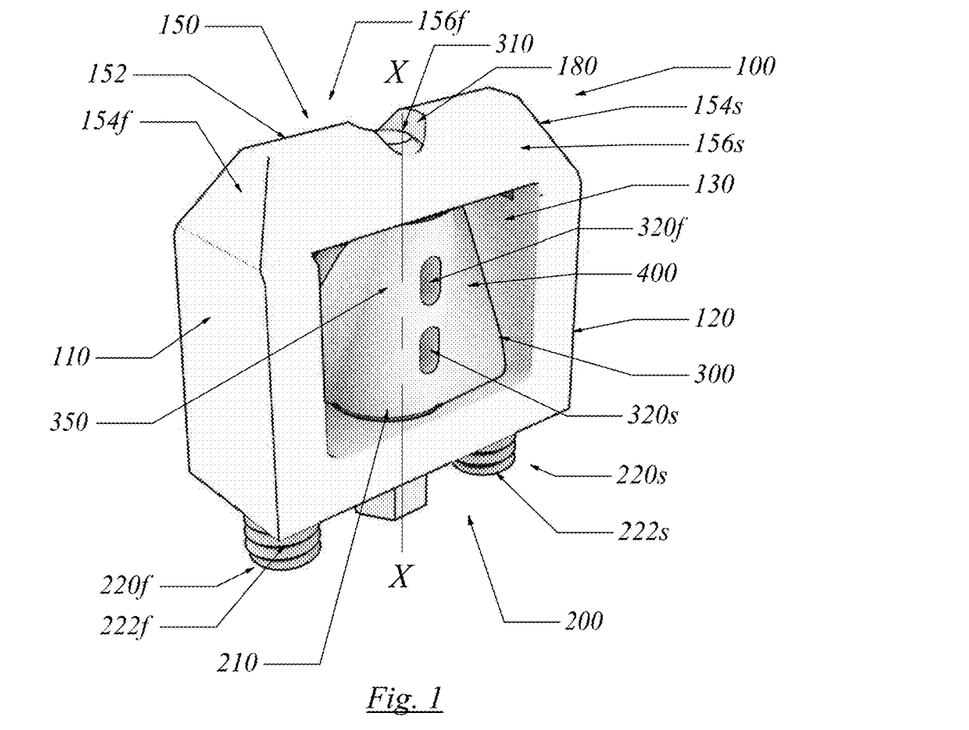
FIG. 1 is a first lateral perspective of a preferred embodiment of biocompatible construction (100).
Figure 2:
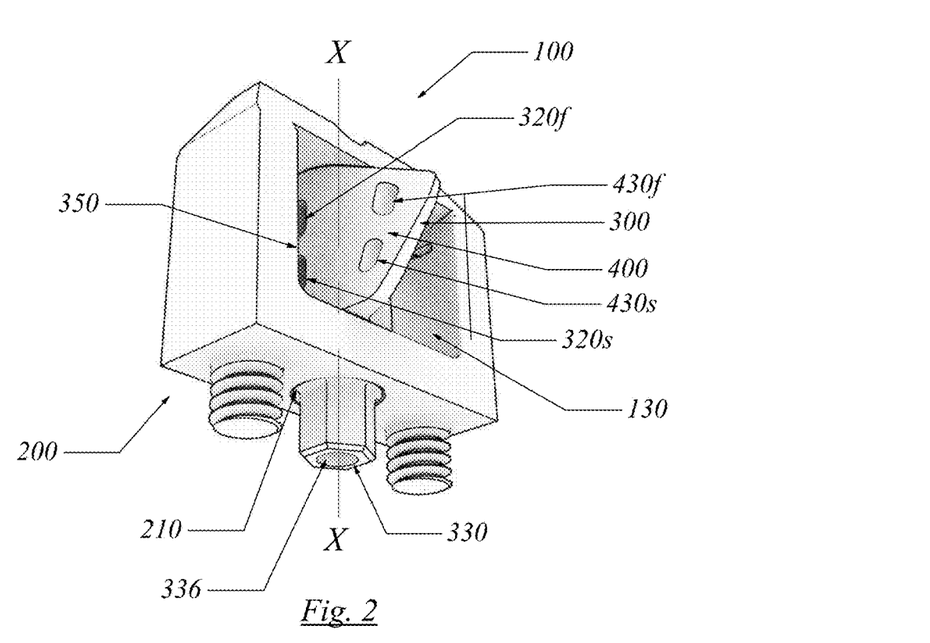
FIG. 2 is a second lateral perspective of the FIG. 1 preferred embodiment of biocompatible construction (100) where cutter (300) was rotated approximately 90 degrees.

FIGS. 1 and 2 are lateral perspectives of biocompatible construction (100). In FIG. 2, cutter 300 was rotated 90 degrees. With reference to FIGS. 1 and 2, biocompatible construction (100) is provided with anterior side (150), surgeon facing side (200), first lateral side (110), second lateral side (120) and rotatable cutter (300).

Anterior side (150) is provided with socket (180) and anterior cutting edge (152). Depending on preselected engineering parameters, socket (180) can extend through anterior side (150). In select preferred embodiments, anterior side (150) can be provided with one or more trapezoidal planes (154f, 154s, 156f, 156s).

Surgeon facing side (200) includes bearing (210) and first and second fittings (220f, 220s). First and second fittings (220f, 220s) are connectable to an insertion tool (not shown in FIGS. 1 and 2). Select embodiments of first and second fittings (220f, 220s) can include threads (222f, 222s).

Biocompatible construction (100) includes longitudinal axis X-X extending through socket (180) and bearing (210). Positioned between anterior side (150), surgeon facing side (200), first lateral side (110), second lateral side (120) are openings (130) lateral to longitudinal axis X-X.

In select preferred embodiments of biocompatible construction (100), lengths of first lateral side (110) and second lateral side (120) are greater than the widths of anterior side (150) and surgeon facing side (200). Such a configuration of biocompatible construction (100) causes longitudinal axis X-X to extend through socket (180) and bearing (210).

Figure 3:
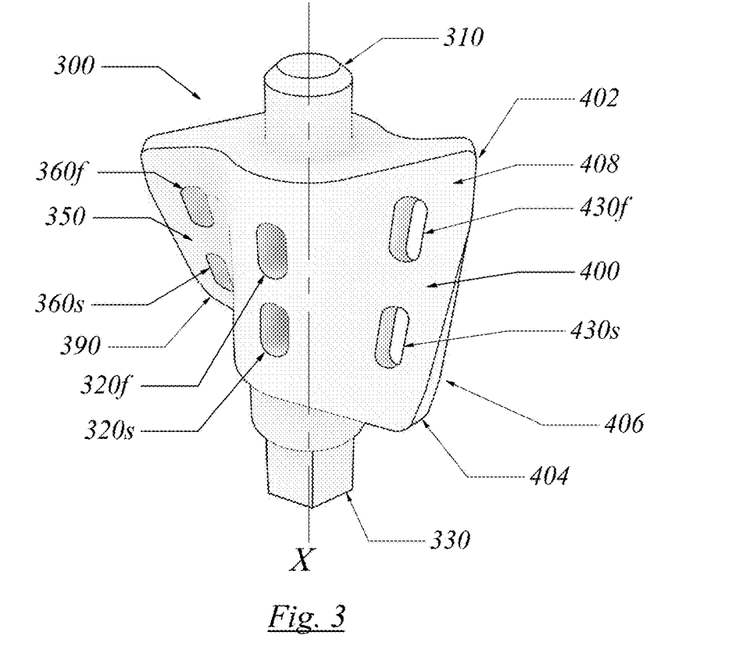
FIG. 3 is a first perspective of a preferred embodiment of rotatable cutter (300).
Figure 4:
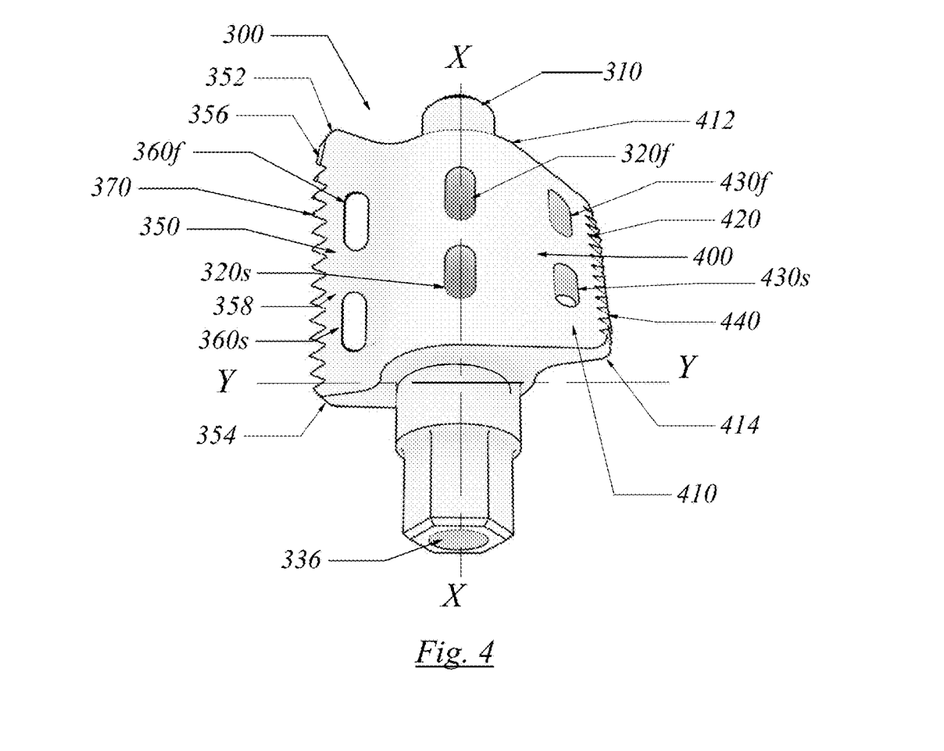
FIG. 4 is another perspective of a preferred embodiment of rotatable cutter (300).

FIGS. 3 and 4 are perspectives of rotatable cutter (300) of biocompatible construction (100). Rotatable cutter (300) is provided with stub axle (310), windows (320f, 320s), connector (330), first section (350) and second section (400). Preferred embodiments of first section (350) and second section (400) can include teeth (370, 440). In other select preferred embodiments, first section (350) is provided with one or more apertures (360f, 360s) and second section (400) is provided with one or more apertures (430f, 430s).

Regarding biocompatible construction (100) shown in FIGS. 1-6, stub axle (310) engages socket (180). According to predetermined engineering parameters, connector (330) can extend outward from bearing (210) toward the surgeon.

In select preferred embodiments of the current invention, connector (330) can include a conduit (336) that, among other things, can provide a pathway for biocompatible medical devices and biocompatible osteogenic and/or other substances into or out of the interior volume of implantation into a created cavity. In select preferred embodiments of the current invention, stub axle (310) and connector (330) can surround longitudinal axis X-X. Connector (330) is connectable to a device (not shown) to rotate rotatable cutter (300).

Windows (320f, 320s) can be aligned with the longitudinal axis X-X, disposed between first section (350) and second section (400) and positioned between stub axle (310) and connector (330). For select preferred embodiments of rotatable cutter (300), stub axle (310), connector (330), first section (350) and second section (400) can be formed as an integral cutting unit.

First section (350) is disposed on a first side of longitudinal axis X-X and second section (400) is disposed on a second side of longitudinal axis X-X. For select preferred embodiments of rotatable cutter (300), first section (350) and second section (400) are opposed from each other in the same identical plane traverse to longitudinal axis X-X. Rotatable cutter (300) can include first section (350) extending from about anterior side (150) to about surgeon facing side (200) and second section (400) extending from about anterior side (150) to about surgeon facing side (200).

Figure 5:
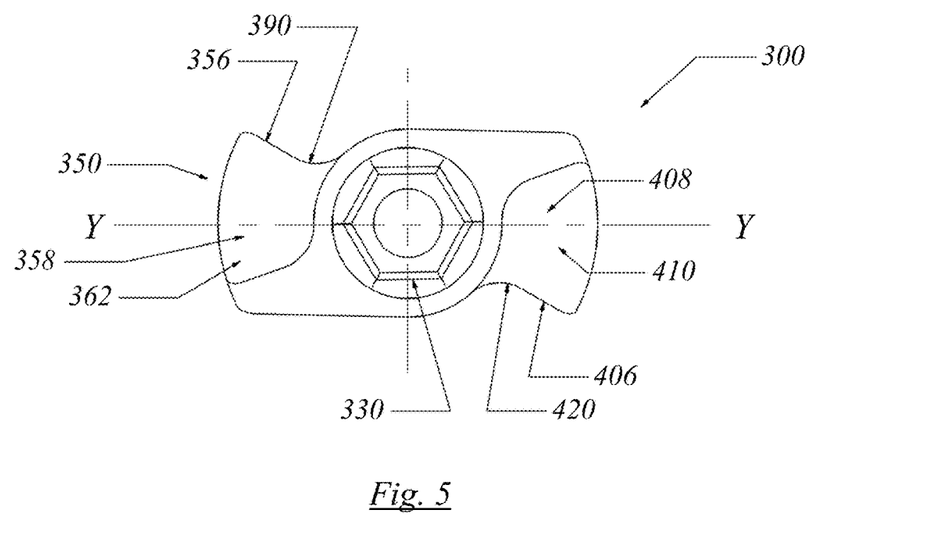
FIG. 5 is a cross-section of FIG. 3 along axis Y-Y that shows concave bends of first section (350) and second section (400) of rotatable cutter (300).

First section (350) includes a first lengthwise end (352) and an opposed second lengthwise end (354). First section (350) is also provided with a first blade (356) to cut a biological structure or tissue and a first noncutting edge (358) opposed to first blade (356). As best shown in FIG. 5, first blade (356) can be provided with a concave bend (390) relative to opposed first noncutting edge (358). In select preferred embodiments of biocompatible construction (100), first blade (356) is provided with serrations or teeth (370) or a combination thereof. In a first plane distinct from concave bend (390), first section (350) can include a first curvature (362) extending between the first lengthwise end (352) and the second lengthwise end (354). In select preferred embodiments of biocompatible construction (100), relative to longitudinal axis X-X, the first curvature (362) curves from a first point more proximate the longitudinal axis X-X toward a second point more distance from the longitudinal axis X-X. Among other things, it is believed that combination of concave bend (390) and first curvature (362) allows for graduated cutting of biological structures.

Second section (400) includes a first lengthwise end (402) and an opposed second lengthwise end (404). Second section (400) is also provided with a second blade (406) to cut a biological structure or tissue and a second noncutting edge (408) opposed to second blade (406). As best shown in FIG. 5, second blade (406) can be provided with a concave bend (420) relative to opposed second noncutting edge (408). In select preferred embodiments of biocompatible construction (100), second blade (406) is provided with teeth (440). In a first plane distinct from concave bend (420), second section (400) can include a first curvature (410) extending between the second lengthwise end (412) and the second lengthwise end (414). In select preferred embodiments of biocompatible construction (100), relative to longitudinal axis X-X, the first curvature (410) curves from a first point more proximate the longitudinal axis X-X toward a second point more distance from the longitudinal axis X-X. Among other things, it is believed that combination of concave bend (420) and first curvature (410) allows for graduated cutting of biological structures.

Figure 6:
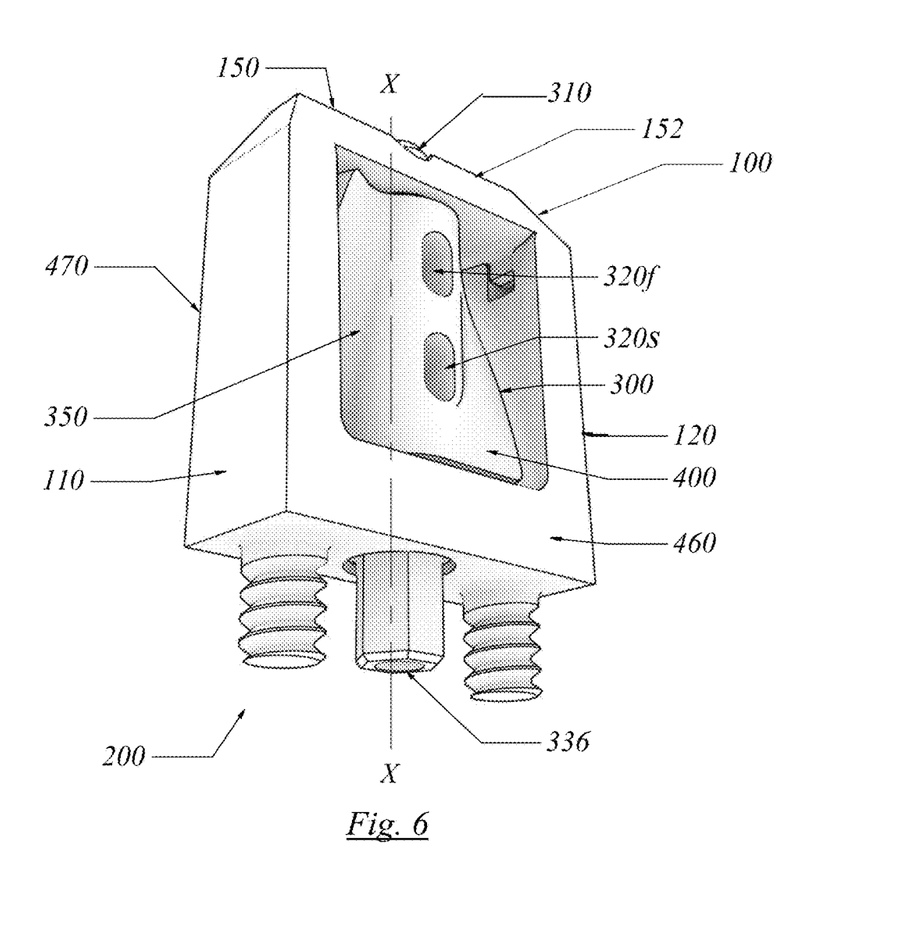
FIG. 6 is a perspective of a preferred embodiment of biocompatible construction (100) with trapezoidal first face (460) and trapezoidal second face (470).

As shown in FIG. 6, a preferred embodiment of biocompatible construction (100) can be provided with anterior side (150) where, in a first direction, anterior side (150) is of lessor length than surgeon facing side (200) such that the anterior side (150), surgeon facing side (200), first lateral side (110) and second lateral side (120) form a trapezoidal first face (460) and a trapezoidal second face (470).

Figure 7:
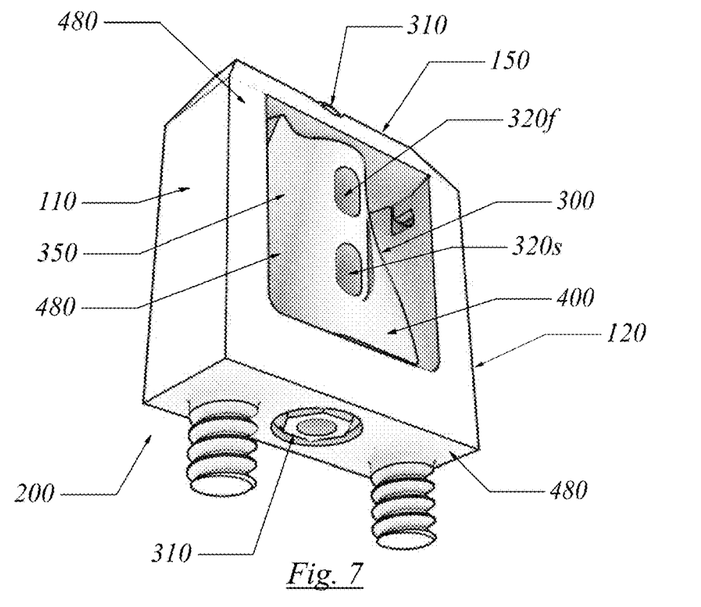
FIG. 7 is a perspective of a preferred embodiment of biocompatible construction (100) with surface treatments (480)

FIG. 7 is a perspective of a preferred embodiment of biocompatible construction (100) with surface treatments (480) such as micropores and/or barbs, etc. applied to anterior cutting edge (150), surgeon facing side (200), first lateral side (110), second lateral side (120) and rotatable cutter (300). It is believed that surface treatments (480) can assist with long term fixation of biocompatible construction (100) by allowing more bone ingrowth into biocompatible construction (100). Surface treatments (480) can be created by abrasive devices, chemical, laser, metal or abrasive particles incorporated into or onto the biocompatible composition or by other means acceptable in the art.

Figure 8:
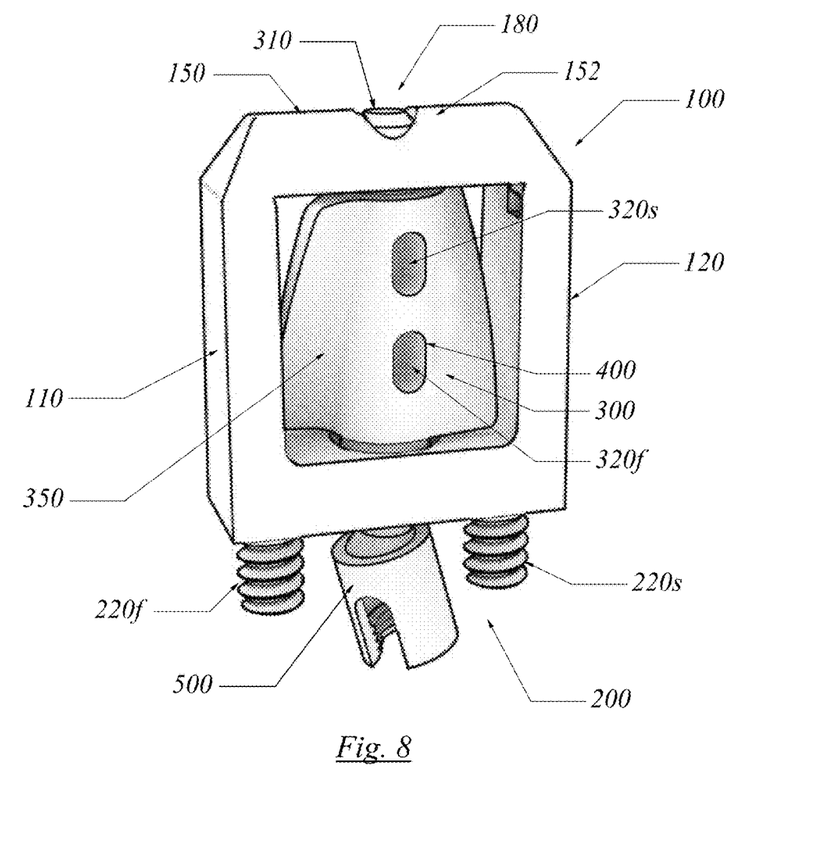
FIG. 8 is a perspective of biocompatible construction (100) provided with polyaxial adapter (500).

As shown in FIG. 8, biocompatible construction (100) is provided with polyaxial adapter (500) connectable to a device (not shown) distinct from biocompatible construction (100).

Figure 9:
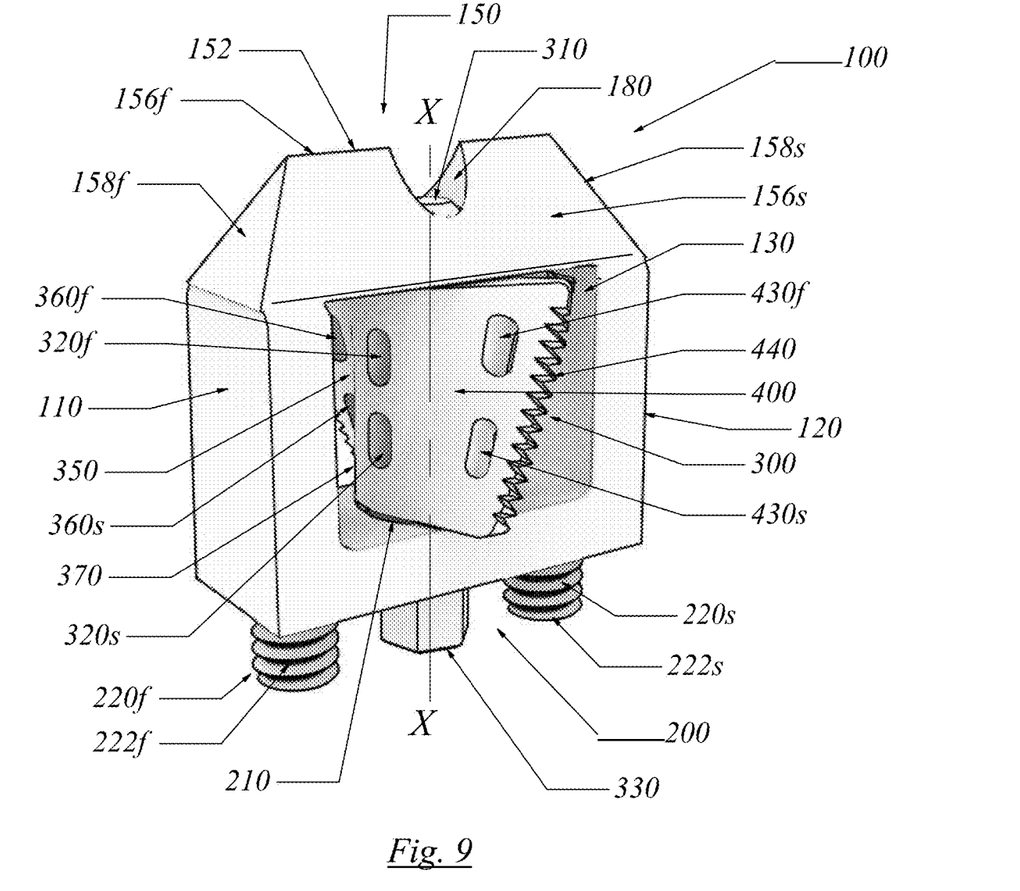
FIG. 9 is a perspective of rotatable cutter (300) and biocompatible construction (100).

FIG. 9 is a perspective of rotatable cutter (300) and biocompatible construction (100). Along with rotatable cutter (300), biocompatible construction (100) is provided with anterior side (150), surgeon facing side (200), first lateral side (110) and second lateral side (120).

Anterior side (150) is provided with socket (180) and anterior cutting edge (152). Depending on preselected engineering parameters, socket (180) can extend through anterior side (150). In select preferred embodiments, anterior side (150) can be provided with one or more trapezoidal planes (156f, 156s) and one or more triangular planes (158f, 158s).

Surgeon facing side (200) includes bearing (210) and first and second fittings (220f, 220s). First and second fittings (220f, 220s) are connectable to an insertion tool (not shown in FIGS. 1 and 2). Select embodiments of first and second fittings (220f, 220s) can include threads (222f, 222s).

Rotatable cutter (300) is provided with stub axle (310), windows (320f, 320s), connector (330), first section (350) and second section (400). Preferred embodiments of first section (350) and second section (400) can include teeth (370, 440). In other select preferred embodiments, first section (350) is provided with one or more apertures (360f, 360s) and second section (400) is provided with one or more apertures (430f, 430s).

Regarding biocompatible construction (100) shown in FIG. 9, stub axle (310) engages socket (180). According to predetermined engineering parameters, connector (330) can extend outward from bearing (210) toward the surgeon. In select preferred embodiments of the current invention, connector (330) can include a conduit (336) (not shown in FIG. 9) that, among other things, can provide a pathway for biocompatible medical devices and biocompatible osteogenic and/or other substances into or out of the interior volume of implantation into a created cavity. In select preferred embodiments of the current invention, stub axle (310) and connector (330) can surround longitudinal axis X-X. Connector (330) is connectable to a device (not shown) to rotate rotatable cutter (300).

Windows (320f, 320s) can be aligned with the longitudinal axis X-X, disposed between first section (350) and second section (400) and positioned between stub axle (310) and connector (330). For select preferred embodiments of rotatable cutter (300), stub axle (310), connector (330), first section (350) and second section (400) can be formed as an integral cutting unit.

First section (350) is disposed on a first side of longitudinal axis X-X and second section (400) is disposed on a second side of longitudinal axis X-X. For select preferred embodiments of rotatable cutter (300), first section (350) and second section (400) are opposed from each other. Rotatable cutter (300) can include first section (350) extending from about anterior side (150) to about surgeon facing side (200) and second section (400) extending from about anterior side (150) to about surgeon facing side (200).

With the exception of teeth (370, 440) shown in some of the Drawings, first section (350) and second section (400) portrayed in FIG. 9 are identical to the previously disclosed first sections (350) and (400).

As measured along longitudinal axis X-X of biocompatible construction (100), preferred embodiments are provided with anterior cutting edge (152) that can be up to about 30 millimeters in length. The length of biocompatible construction (100), including anterior cutting edge (152) can be from about 6 millimeters to about 50 millimeters. Cross-sectional widths of anterior side (150) can range from about 12 millimeters$^2$ to about 200 millimeters$^2$. Cross-sectional widths of biocompatible construction (100), other than anterior side (150) can range from about 16 millimeters$^2$ to about 320 millimeters$^2$.

Select preferred embodiments of the current invention have been disclosed and enabled as required by Title 35 of the United States Code and/or the Articles of the Patent Cooperation Treaty.

What is claimed is:

1. A biocompatible construction for implantation into a joint or surgically created cavity; the biocompatible construction comprising:
   a) an anterior side comprising an anterior cutting edge and a socket extending therethrough;
   b) a surgeon facing side, opposite the anterior side, comprising a bearing;
   c) a longitudinal axis (X-X) extending through the socket and the bearing, wherein lateral openings of the biocompatible construction are outward from the longitudinal axis (X-X); and
   d) a cutter rotatable about the longitudinal axis (X-X) and adapted to cut a biological structure; the cutter comprising:
      i) a stub axle, surrounding the longitudinal axis (X-X), engaging the socket;
      ii) a connector, surrounding the longitudinal axis (X-X) and distinct from the stub axle; the connector contacting the bearing and connectable to a device adapted to rotate the cutter;
      iii) windows aligned with the longitudinal axis (X-X) and positioned between the stub axle and the connector;
      iv) a first section, on a first side of the longitudinal axis (X-X), extending lengthwise between the anterior side and the surgeon facing side and a second section, on an opposed second side of the longitudinal axis (X-X), extending lengthwise between the anterior side and the surgeon facing side;
      v) the first section comprising:
         a first cutting blade to cut the structure and a first noncutting edge opposed from the first cutting blade, wherein the first cutting blade comprises a concave bend relative to the opposed first noncutting edge;
         a first curvature between a first lengthwise end and an opposed second lengthwise end of the first noncutting edge, wherein, relative to the longitudinal axis (X-X), the first curvature curves from a first point more proximate to the longitudinal axis (X-X) to a second point more distant from the longitudinal axis (X-X); and
      vi) the second section comprising:
         a second cutting blade to cut the structure and a second noncutting edge opposed from the second cutting blade, wherein the second cutting blade comprises a concave bend relative to the opposed second noncutting edge; and
         a second curvature between a first lengthwise end and an opposed second lengthwise end of the second noncutting edge, wherein, relative to the longitudinal axis (X-X), the second curvature curves from a first point more proximate to the longitudinal axis (X-X) to a second point more distant from the longitudinal axis (X-X).

2. The biocompatible construction of claim 1, wherein the connector comprises a polyaxial adapter connectable to the biocompatible construction; the polyaxial adapter adapted to receive the device adapted to rotate the cutter.

3. The biocompatible construction of claim 2, wherein the first cutting blade and the second cutting blade comprise teeth.

4. The biocompatible construction of claim 3, wherein:
   a) the first section comprises one or more apertures positioned laterally between the windows and the first curvature; and
   b) the second section comprises one or more apertures positioned laterally between the windows and the second curvature.

5. The biocompatible construction of claim 4, wherein the anterior side in a first direction is of lesser length than the surgeon facing side such that the anterior side, surgeon facing side, first lateral side and second lateral side form a trapezoidal first face and a trapezoidal second face.

6. The biocompatible construction of claim 5, wherein, in a second direction distinct from the first direction, a combination of the anterior side, surgeon facing side, the first lateral side and second lateral side create trapezoidal lateral sides distinct from the trapezoidal first face and the trapezoidal second face.

7. The biocompatible construction of claim 6, wherein the surgeon facing side comprises first and second fittings connectable to an insertion device.

8. A biocompatible construction for implantation into a joint or a surgically created cavity; the biocompatible construction comprising:
   a) an anterior side comprising an anterior cutting edge and a socket extending therethrough;
   b) a surgeon facing side, opposite the anterior side, comprising a bearing;
   c) a longitudinal axis (X-X) extending through the socket and the bearing, wherein lateral openings of the biocompatible construction are outward from the longitudinal axis (X-X); and
   d) a cutter rotatable about the longitudinal axis (X-X) and adapted to cut a structure; the cutter comprising:
      i) a stub axle engaging the socket;
      ii) a connector contacting the bearing and connectable to a device adapted to rotate the cutter;
      iii) first and second interconnected sections on opposite sides of the longitudinal axis (X-X); the first and second interconnected sections extending lengthwise between the anterior side and the surgeon facing side, wherein each interconnected section comprises a blade to cut a structure and a noncutting edge opposed from the blade; and iv) at least one window aligned with the longitudinal axis (X-X) and positioned between the stub axle and the connector.

9. The biocompatible construction of claim 8, wherein the connector comprises a conduit extending from the surgeon facing side to the window.

10. The biocompatible construction of claim 9, wherein each blade comprises teeth.

11. The biocompatible construction of claim 10, wherein each interconnected section comprises at least one aperture positioned between the at least one window and a first curvature of the first section and a second curvature of the second section.

12. The biocompatible construction of claim 11, wherein the anterior side comprises at least two trapezoidal planes.

13. The biocompatible construction of claim 12, wherein each interconnected section comprises:
 a) a concave bend relative to the opposed noncutting edge; and
 b) a curve between a first lengthwise end and an opposed second lengthwise end of the blade, wherein, relative to the longitudinal axis (X-X), the opposed noncutting edge curves from a first point more proximate to the longitudinal axis (X-X) to a second point more distant from the longitudinal axis (X-X).

14. The biocompatible construction of claim 13, wherein the connector comprises a polyaxial adapter connectable to the device distinct from the biocompatible construction.

15. The biocompatible construction of claim 14, wherein, in a first direction, the anterior side is of lesser length than the surgeon facing side such that the anterior side, surgeon facing side, first lateral side and second lateral side form a trapezoidal first face and a trapezoidal second face.

16. The biocompatible construction of claim 15, wherein, in a second direction distinct from the first direction, a combination of the anterior side, surgeon facing side, the first lateral side and second lateral side create trapezoidal lateral sides distinct from the trapezoidal first face and the trapezoidal second face.

17. A biocompatible construction for implantation into a joint or surgically created cavity; the biocompatible construction comprising:
 a) an anterior side comprising an anterior cutting edge and a socket extending therethrough; the anterior side comprising at least two trapezoidal planes;
 b) a surgeon facing side, opposite the anterior side, comprising a bearing;
 c) lateral openings of the biocompatible construction positioned outward from a longitudinal axis (X-X); and
 d) a rotatable cutter adapted to cut a biological structure; the cutter comprising:
  i) a stub axle engaging the socket;
  ii) a connector, engaging the bearing, connectable to a device adapted to rotate the cutter;
  iii) first and second sections on opposite sides of the longitudinal axis (X-X); the first and second sections extending lengthwise between the stub axle and the connector, wherein each section comprises:
   a blade to cut the biological structure and a noncutting edge opposed from the blade; and
   a curvature between a first lengthwise end and an opposed second lengthwise end of the noncutting edge, wherein, relative to the longitudinal axis (X-X), the opposed noncutting edge curves from a first point more proximate to the longitudinal axis (X-X) to a second point more distant from the longitudinal axis (X-X).

18. The biocompatible construction of claim 17, wherein each of the first and second sections comprises a concave bend relative to the opposed noncutting edge.

19. The biocompatible construction of claim 18 comprising a window disposed within the interconnected first and second sections.

20. The biocompatible construction of claim 19, wherein each blade comprises teeth.

21. The biocompatible construction of claim 20, wherein the connector comprises a conduit extending from the surgeon facing side to the window.

22. The biocompatible construction of claim 21, wherein the connector comprises a polyaxial head connectable to the device adapted to rotate the cutter.

23. The biocompatible construction of claim 22, wherein, in a first direction, the anterior side is of lesser length than the surgeon facing side such that the anterior side, surgeon facing side, first lateral side and second lateral side form a trapezoidal first face and a trapezoidal second face.

24. The biocompatible construction of claim 23, wherein, in a second direction distinct from the first direction, a combination of the anterior side, surgeon facing side, the first lateral side and second lateral side create trapezoidal lateral sides distinct from the trapezoidal first face and the trapezoidal second face.

\* \* \* \* \*